United States Patent [19]
Goodsall et al.

[11] Patent Number: 6,113,965
[45] Date of Patent: Sep. 5, 2000

[54] PRODUCING THEAFLAVIN

[75] Inventors: Christopher William Goodsall; Andrew David Parry; Richard Safford; Ambalavanar Thiru, all of Bedford, United Kingdom

[73] Assignee: Lipton, Division of Conopco, Inc., Englewood Cliffs, N.J.

[21] Appl. No.: 09/115,961

[22] Filed: Jul. 15, 1998

[30] Foreign Application Priority Data

Jul. 15, 1997 [EP] European Pat. Off. .............. 97305259

[51] Int. Cl.[7] ................................ A23L 1/28; A23L 1/20; A23B 7/10; A23F 3/34; A23F 3/00
[52] U.S. Cl. ............... 426/425; 426/49; 426/429; 426/431; 426/435; 426/597
[58] Field of Search .............. 426/597, 99, 929, 426/435, 431, 425

[56] References Cited

U.S. PATENT DOCUMENTS 3,812,266  5/1974  Sanderson et al. ................ 426/52
4,051,264  9/1977  Sanderson et al. ................ 426/52
5,532,012  7/1996  Ballentine et al. ................ 426/425

FOREIGN PATENT DOCUMENTS 760 213  3/1997  European Pat. Off. .

OTHER PUBLICATIONS

Database Abstract. AN 71(09):H1308 FSTA. Journal of Chromatography. vol. 57, No. 1, pp. 19–27. Authors: Collier et al., 1971.

European Search Report in the application of EP 97 30 5259 dated Dec. 11, 1997.

*Primary Examiner*—Anthony J. Weier
*Attorney, Agent, or Firm*—James J. Farrell

[57] ABSTRACT

Theaflavin is produced by separating theaflavin from a slurry fermentation product of green leaf tea that has been treated with tannase prior to slurry fermentation. Methods for making theaflavin-rich extracts and cold water soluble tea powders and products are provided.

11 Claims, 12 Drawing Sheets

(−)-Epicatechin [EC]

(−)-Epigallocatechin [EGC]

(−)-Epicatechin-3-gallate [ECG]

(−)-Epigallocatechin-3-gallate [EGCG]

Gallic acid [GA]

Fig.1.
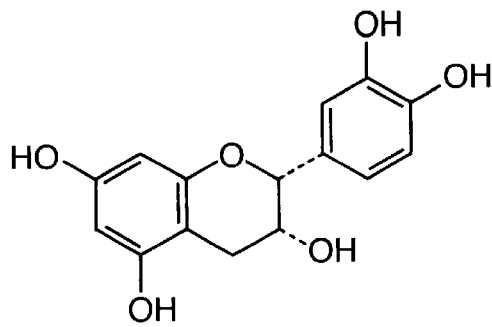
(-)-Epicatechin [EC]
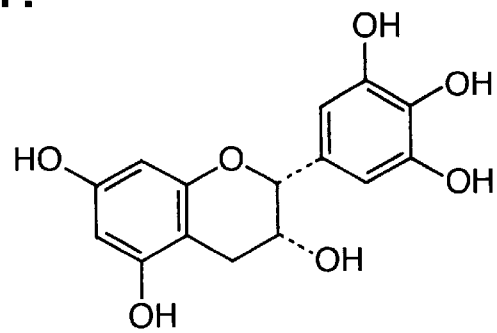
(-)-Epigallocatechin [EGC]
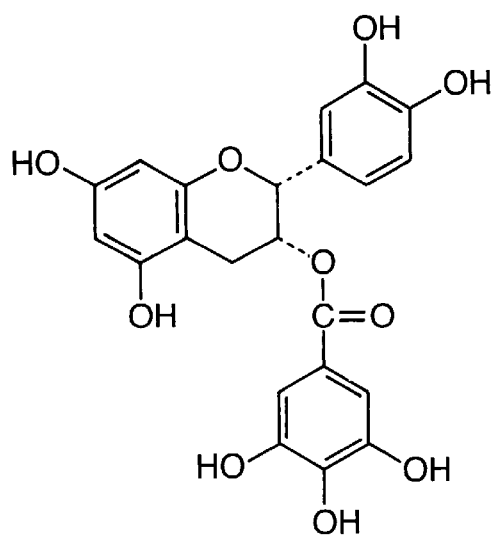
(-)-Epicatechin-3-gallate [ECG]
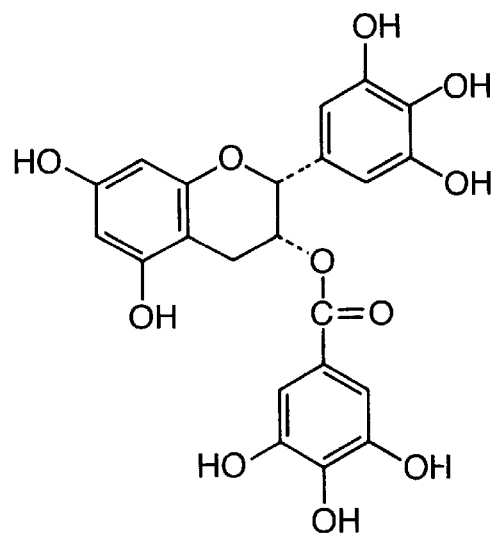
(-)-Epigallocatechin-3-gallate [EGCG]
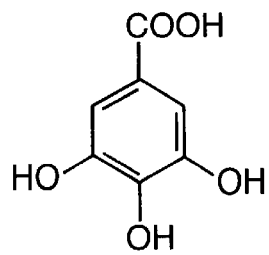
Gallic acid [GA]

Fig.2.
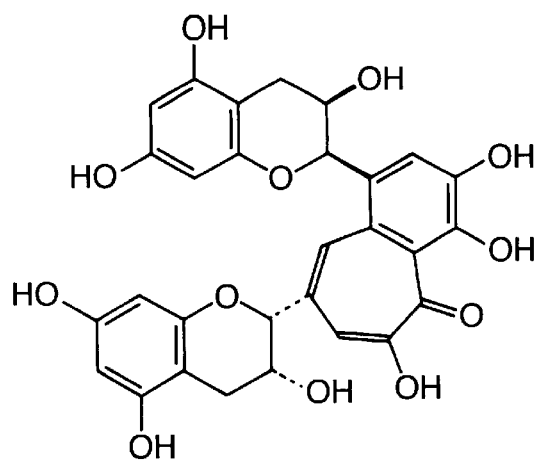
Theaflavin (EC+EGC)
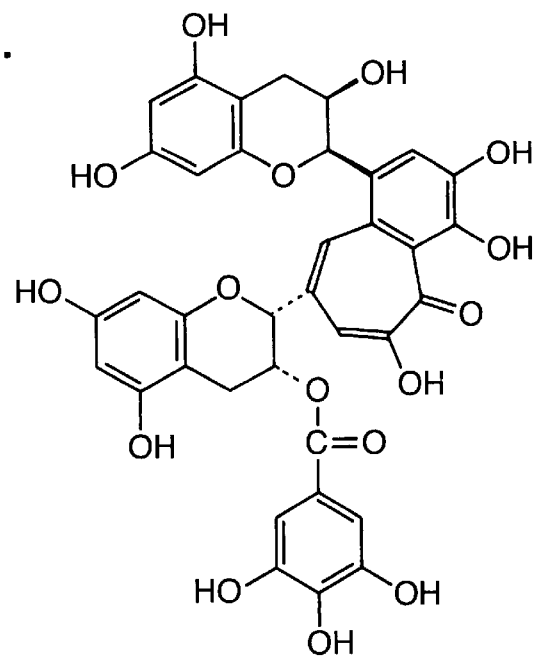
Theaflavin-3-gallate (EC+EGCG)
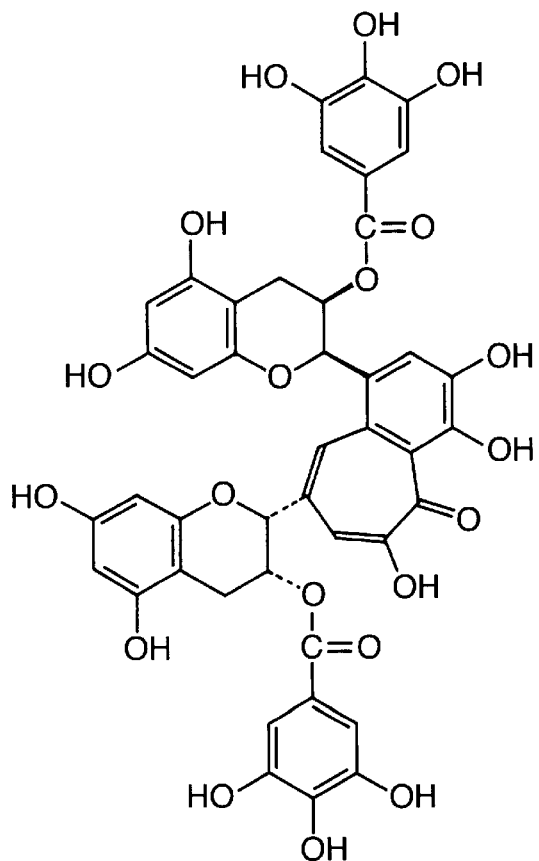
Theaflavin-3,3'-digallate (ECG+EGCG)
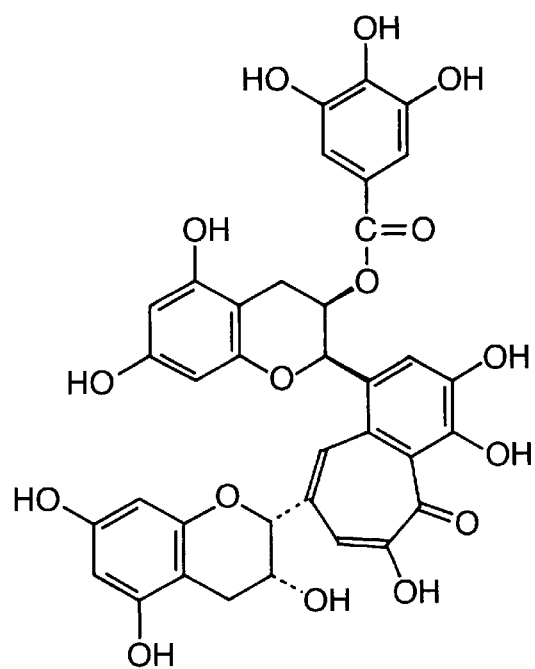
Theaflavin-3'-gallate (ECG+EGC)

PRODUCING THEAFLAVIN

FIELD OF INVENTION

This invention concerns the production of theaflavin, one of a class of coloured polyphenols that are produced during the oxidative fermentation of green tea leaf. The invention provides a method for making theaflavin and a method for making cold water soluble tea powders that have enhanced levels of theaflavin.

BACKGROUND TO THE INVENTION

Green tea leaf (as picked) contains colourless polyphenols known as catechins. The four major catechins in green tea leaf are epicatechin (EC) and epigallocatechin (EGC) and the gallated forms of these catechins (bearing a gallic acid (GA) residue), epicatechin-3-gallate (ECG) and epigallocatechin-3-gallate (EGCG). The structures of these compounds are shown in FIG. 1.

During oxidative fermentation of green leaf to produce black tea (either solid state fermentation to produce black leaf or slurry fermentation to produce black tea extracts) the catechins undergo oxidative biotransformations, through their quinones, into dimeric compounds known as theaflavins (TFs) and higher molecular weight compounds known as thearubigins (TRs). TFs and TRs are responsible for the orange and brown colours of black tea infusions and products as well as making significant contributions to the astringency and body of the made tea. TRs are larger in size and darker in colour than TFs. The oxidative polymerisations are a combination of biochemical oxidations mediated by polyphenol oxidase and/or peroxidase enzymes present in the leaf and chemical reactions of reactive species. TFs include theaflavin (TF or TF1) and a range of related gallated derivatives, the structures of some of which are shown in FIG. 2.

Theaflavin and theaflavins have been recognised as providing the "brightness" and "briskness" quality attributes of tea. They also affect tea colour. Most theaflavins have antioxidant properties and are therefore of great interest to the food and health industries.

U.S. Pat. No. 5,532,012 (Ballentine et al) describes extraction from tea cream (cold water insoluble material resulting from infusion of black tea with hot water) of a mixture of theaflavins closely approximating the natural mixture of theaflavins found in tea cream. The mixture of theaflavins extracted comprises theaflavin, theaflavin monogallates and theaflavin digallate.

The present invention is concerned with producing theaflavin by slurry fermenation and cold water soluble tea powders that have enhanced theaflavin levels.

STATEMENT OF THE INVENTION

In a first aspect, the present invention in broad terms relates to a method for preparing a theaflavin-rich tea extract. The method comprises treating a slurry of green leaf tea with tannase and fermenting the slurry to yield a theaflavin-rich tea extract.

In a second aspect, the present invention relates to a method for making a theaflavin-rich cold water soluble tea powder. The method comprises treating a slurry of green leaf tea with tannase, fermenting the slurry, deleafing the slurry to give a theaflavin-rich tea liquor, and drying the tea liquor to yield a theaflavin-rich cold water soluble tea powder.

In a third aspect, the present invention relates to a method for making a theaflavin-rich cold water soluble tea product. The method comprises treating a slurry of green leaf tea with tannase, fermenting the slurry, deleafing the slurry to give a theaflavin-rich tea liquor and spent dhool, drying the tea liquor to yield a liquor-derived theaflavin-rich cold water soluble tea powder, performing one or more solvent extractions of the spent dhool, drying the extract or extractions to form a dhool-derived theaflavin-rich powder or powders, and mixing the liquor-derived theaflavin-rich cold water soluble tea powder with the dhool-derived theaflavin-rich powder or powders to yield a theaflavin-rich cold water soluble tea product.

Alternatively one could mix the liquor-derived and dhool-derived theaflavin-rich extracts prior to drying and forming a theaflavin-rich powder.

Preferably the solvent is water or an organic solvent. Sequential washes of cold water (15 to 25° C.), hot water (90 to 100° C.) and methanol are especially preferred.

In a fourth aspect, the present invention relates to a method of producing theaflavin. The method comprises treating green leaf tea with tannase prior to slurry fermentation, performing slurry fermentation, and separating theaflavin from the product of slurry fermentation.

In a fifth aspect, the present invention relates to a method for purifying theaflavin. The method comprises treating a slurry of green leaf tea with tannase, fermenting the slurry, deleafing the slurry to give a theaflavin-rich tea liquor and spent dhool, drying the tea liquor to yield a theaflavin-rich cold water soluble tea powder, resuspending the powder in water, extracting the resuspended powder with an organic solvent, and passing the extracted powder through a chromatographic column that elutes theaflavin.

In a sixth aspect, the present invention relates to a method for purifying theaflavin. The method comprises treating a slurry of green leaf tea with tannase, fermenting the slurry, deleafing the slurry to give a theaflavin-rich tea liquor and spent dhool, drying the tea liquor to yield a liquor-derived theaflavin-rich cold water soluble tea powder, performing one or more solvent extractions of the spent dhool, drying the extract or extractions to form a dhool-derived theaflavin-rich powder or powders, mixing the liquor-derived theaflavin-rich cold water soluble tea powder with the dhool-derived theaflavin-rich powder or powders to give a theaflavin-rich cold water soluble tea product, resuspending the tea product in water, extracting the resuspended product with an organic solvent, and passing the extracted product through a chromatographic column that elutes theaflavin.

Alternatively, one could mix the liquor-derived and dhool-derived theaflavin-rich extracts prior to drying and forming a theaflavin-rich powder.

"Tea" for the purposes of the present invention means leaf material from *Camellia sinsensis* or *Camellia assamica*. "Tea is also intended to include the product of blending leaf material from these plants.

"Leaf tea" means a tea product that contains one or more tea origins in an uninfused form.

"Theaflavin" is a chemical compound that is the oxidation and condensation product of (−)-epicatechin and (−)-epigallocatechin. It is also known as TF1 or simply TF. "Theaflavins" collectively describes those compounds (including theaflavin) that are formed by the enzymic oxidation and condensation of tea catechins with di- and trihydroxylated B rings. Some of these compounds are illustrated in FIG. 2. The present invention concerns making extracts, powders and products that are rich in theaflavin rather than theaflavins.

For the avoidance of doubt the word 'comprising' is intended to mean including but not necessarily "consisting of" or "composed of". In other words the listed steps or options need not be exhaustive.

DETAILED DESCRIPTION OF THE INVENTION

The present invention arose from work by the present inventors investigating oxidative biotransformations occurring during tea fermentation, particularly with regard to generation of colour in tea products.

Investigations were made into the use of tannase (flavanol gallate esterase) pretreatment of green tea leaf, prior to slurry fermentation, as this is known to lead to improved redness of slurry fermentation products. The general reaction catalysed by tannase is the cleavage of gallate ester linkages, both on gallated catechins and also from other gallated compounds within the leaf. Tannase is well known to improve the clarity of tea products since galloyl groups are important in cream formation and tannase has been used extensively for the degallation and solubilisation of black tea cream. The use of tannase for pretreatment of green tea prior to slurry fermentations is also disclosed, e.g. in U.S. Pat. No. 3,812,266 (Sanderson et al), where tannase is used with the primary aim of reducing the amount of tea cream in liquors. Improved colours generated by the process were also noted.

Epigallocatechin-3-gallate (EGCG) and epicatechin-3-gallate (ECG) are the most abundant catechins in fresh tea leaves and their gallate ester linkages are cleaved by tannase treatment to yield EGC, EC and gallic acid. The overall effect of tannase pretreatment before slurry fermentation is therefore to simplify the mixture of catechins present at the start of fermentation. It has generally been assumed hitherto that during subsequent oxidation the increased levels of gallic acid combine with simple (dihydroxy B-ring) catechins (e.g. EC) to give rise to high levels of theaflavic acids. Thus, during the synthesis of theaflavic acids, gallic acid acts as the gallocatechin (trihydroxy B-ring) in the synthesis of these TF analogues. Gallic acid will not react with other gallocatechins (ie. EGCG and EGC) to form benzotropolone ring structures. Theaflavic acids are characteristically bright red in colour, so significantly better coloured liquors would be produced as a result of their accumulation. In U.S. Pat. No. 3,812,266, enhanced production of epitheaflavic acid (which has a bright reddish black tea-like colour) is proposed as the explanation for the improved colours generated with tannase pretreatment.

The present inventors have, however, shown that at least in their system this explanation is incorrect, and that the improved colour produced following tannase pretreatment in fact results from production of enhanced levels of theaflavin (See Example 3). Tannase treatment degallates the gallated catechins ECG and EGCG to produce the degallated catechins EC and EGC. On subsequent oxidation during fermentation the catechins EC and EGC react to produce theaflavin, rather than the mixture of theaflavins (as shown in FIG. 2) that would otherwise be produced. Model oxidation studies have shown that EC and EGC react with higher efficiency to form theaflavin than their gallated counterparts. The tannase treatment is therefore preferably such as to cause substantially complete degallation of the gallated catechins in the dhool, in order to maximise production of theaflavin. This showing led the way to a novel method of producing substantially pure theaflavin in high yield. This in turn provided the key for making theaflavin-rich extracts and powders.

In practising the method of the invention, theaflavin is conveniently separated from the slurry fermentation product by solvent extraction, suitably using ethyl acetate, followed by elution from a chromatographic column with ethanol. Theaflavin-rich fractions can be identified by colour.

The slurry fermentation product is typically in the form of a powder. The powder is conveniently mixed with water to form an aqueous solution/suspension that can undergo solvent extraction. Initial extraction is preferably with chloroform, to remove caffeine and lipids, followed by ethyl acetate, to remove theaflavin. Ethyl acetate extracts are typically then washed with water and dried. The dried material may then be dissolved in ethanol and loaded onto a chromatographic column of suitable resin beads, e.g. SEPHADEX (SEPHADEX is a Trade Mark) pre-equilibrated with ethanol, and fractions eluted with ethanol. Theaflavin-rich fractions (identified by colour, and confirmed by HPLC analysis) can be collected and combined.

Other suitable techniques for separating theaflavin from the slurry fermentation product may be employed as desired.

The slurry fermentation product may be produced by generally conventional techniques, as are well known to those skilled in the art, e.g. generally as disclosed in the U.S. Pat. No. 3,812,266. Slurry fermentation typically involves treating dhool (a slurry of macerated withered green tea leaf) by bubbling air or oxygen through the slurry for a controlled time at a controlled temperature, e.g. 25° C., resulting in oxidative biotransformations taking place as described above. Solids are removed from the slurry (deleafing), optionally concentrated, and the liquid is then dried, e.g. spray or freeze dried, to produce a powder or granules.

Prior to slurry fermentation, the dhool is treated with tannase. This is conveniently effected by mixing the dhool and tannase in suspension in an atmosphere of nitrogen (to prevent fermentation occurring) for a suitable time at a suitable temperature. Suitable conditions can be readily determined by experiment. Good results have been obtained with KIKKOMAN's tannase (KIKKOMAN is a trade mark) in an amount of at least about 0.0064% by weight of the weight of tea solids (i.e. 3200 tannase activity units (T.A.U.)/kg tea solids wherein tea leaf solids content is determined after measuring the moisture content of the leaf. KIKKOMAN's tannase has 50,000 T.A.U/gram) for 60 minutes at 25° C., which results in quantitative degallation of gallated catechins.

The slurry fermentation conditions are preferably adjusted to maximise production of theaflavin as far as possible.

Fermentation is preferably carried out at a pH in the range of 4.0 to 5.5. The fermentation temperature is preferably in the range 15 to 35° C. Fermentation is preferably carried out for a time in the range 30 to 120 minutes, more preferably 30 to 75 minutes. To maximise TF production, fermentation should be stopped when EGC has been used up, as after this theaflavin levels fall due to oxidation by residual EC. Fermentation should also be carried out without addition of hydrogen peroxide (as is used in U.S. Pat. No. 3,812,266) as this destroys theaflavin (while enhancing overall colour). Similarly enzymes such as exogenous peroxidases, laccases and polyphenol oxidases should not be present as these would reduce theaflavin levels.

The green leaf starting material may also be selected to optimise theaflavin production. The preferred starting material has an EGC(G): EC(G) ratio of about 3:1 (See Example 3). Although 1 mole of EGC reacts with 1 mole or EC (after degallation), differential oxidation rates mean that 3:1 is the preferred molar ratio. Tea clones having a suitable molar ratio can be selected with this requirement in mind.

The present invention can enable production of substantially pure theaflavin in high yields. Theaflavin yields at least 11 times those obtained without tannase treatment have been achieved in accordance with the method of the invention in its simplest form. Theaflavin yields of at least 11 g TF/kg dhool are achievable by that method.

Initial studies of the time course of slurry fermentation, based on compositional analysis of the aqueous phase, showed that TF levels peaked and then decreased with fermentation time, implying either that TF oxidation was occurring or that TF was binding to the cellular material. In model system studies, TF accumulated rapidly and was then stable (See Example 3). This suggested that TF was binding to the leaf material during the slurry fermentation rather than being oxidised.

An exhaustive extraction protocol was therefore developed to enable a more complete recovery of TF from slurry mixtures (See Example 4). The use of this extraction procedure showed that TF was not being oxidised during fermentation but was actually associating with the dhool. In fact, comparison of the EC levels in the liquor with the peak levels of TF revealed that TF formation was around the theoretical maximum and that there was little 'residual' EC available to oxidise TF.

The improved extraction procedure showed that considerable additional TF could be obtained from tannase-treated slurries by employing a combination of cold and hot water washes of the dhool, after removal of the liquor. "Cold water" means water having a temperature between 15 and 25° C., this could preferably be room temperature. "Hot water" means water having a temperature between 90 and 100° C., preferably freshly boiled water. Overall about 90% of TF could be recovered by combining the liquor with the cold and hot water washes, compared to only 30% in the liquor alone.

The improved extraction method was used to optimise fermentation conditions (temperature—see Example 5, and pH—see Example 6) in order to maximise TF yield from tannase-treated slurry fermentation. When total TF levels were considered, pH 4.0 and 15° C. were found to be the optimum operating conditions, although the benefit gained under these conditions was minor compared to 'natural' fermentation conditions. However, temperature did effect the amount of theaflavin present in the liquor phase of the slurry, the proportion increasing with fermentation temperature.

The mechanism whereby TF is bound to the dhool is unclear. While not wanting to be bound by theory, results from tannase-treated fermentations suggest that, under a variety of different conditions, the amount of TF found in the hot water and solvent fractions (i.e. the most strongly bound TF) is fairly constant and that the differences in total TF are reflected in relative amounts of TF present in the liquor and cold water (loosely bound TF) fractions. This might imply that TF binds preferentially to some 'high affinity' sites on the dhool and that when they become 'saturated' the remaining TF becomes either loosely bound (cold water fraction) or is in solution in the liquor. The balance of TF between these two latter fractions is affected by the temperature of the fermentation, i.e. at higher temperatures a greater proportion of TF is present in the liquor phase. An attempt to ferment at the optimum temperature (15° C.) for TF production and then heat the slurry to 35° C. to 'release' more TF into the liquor only produced a marginal improvement over a regular 15° C. fermentation. This would imply that once 'bound', TF is not easily removed.

The additional material that can be released from the spent dhool with cold and hot water is intensely coloured and proportionally much higher in TF content than the liquor. This material can be used to blend into powder products to add more/different colour or be combined with the slurry liquor to produce a cold water-soluble powder which is considerably darker and redder than that produced from liquor alone. Slurry fermentation thus provides a means of producing cost-effective, natural cold and hot water-soluble tea powders.

Regarding the use of tannase slurry as a route for TF production, the maximum extraction data revealed that formation of 200 $\mu$mol of TF from 8 g (FW) of dhool is possible, this corresponds to formation of 14.1 g TF/kg (FW) dhool. With the optimised process cold water soluble tea powders, containing 11.7% TF by mass were generated (See Table 8 of Example 8). This corresponds to a final yield of 11 g TF/kg (FW) dhool.

As previously mentioned, theaflavin is known to affect the colour, "brightness" and "briskness" of tea. Because of its antioxidant properties, theaflavin (and perhaps other theaflavins) has potential uses including as an antioxidant ingredient in foodstuffs such as processed foods and oils, as an ingredient in health-promoting products, and as ingredient in tea products for colour properties as well as antioxidant properties. For example, food materials that may to advantage incorporate theaflavin produced by the method of the invention as an antioxidant ingredient include frying oils and fats, potato flakes, bakery products, meat emulsions, precooked cereals, instant noodles, soy bean milk, chicken products, emulsion products such as sausage, mayonnaise and margarine, frozen fish, frozen pizza, cheese and animal foods.

The invention will be further described, by way of illustration, in the following Examples and with reference to the accompanying drawings on which:

FIG. 1 shows the chemical structure of various catechins present in green tea leaf;

FIG. 2 shows the chemical structure of theaflavin and various gallated theaflavins;

EXAMPLE 1

Production of Theaflavin in Tannase-treated Slurry Fermentation and Subsequent Isolation in High Purity Raw Material Fresh Kenyan tea (Clone BBK 35) was plucked and withered overnight, then frozen in dry ice and transported to UK.

Fermentation

Withered leaf was macerated by 3 passes through a CTC (Crush/Tear/Curl) machine and the resulting dhool suspended in a 5 l slurry fermenter (388 g leaf/2.5 l water) under nitrogen sparge (to prevent fermentation) for 60 minutes at 25° C. in the presence of 10 mg KIKKOMAN's tannase (KIKKOMAN is a trade mark). These conditions result in quantitative degallation of gallated catechins. Fermentation is allowed to proceed for 60 minutes with an air flow rate of 1 l/min and agitating the suspension at 625 rpm.

TF Extraction/Purification

The fermentation liquor was deleafed by passage through 4 layers of muslin. The residual dhool was washed with 500 ml distilled water, and the wash and liquor combined, cooled to 4° C., centrifuged and the supernatant freeze-dried using a pilot scale freeze dryer. This yielded approximately 25 g of powder.

Lab scale TF purification was as follows. 5 g of the powder were resuspended in 100 ml water, and stirred until completely dissolved. The aqueous fraction was then extracted successively with 100 ml hexane, 2×100 ml chloroform and 4×100 ml ethyl acetate. The hexane removes lipid. The chloroform removes caffeine and any residual lipid. The ethyl acetate fractions were combined and re-extracted with an equal volume of water. The ethyl acetate fraction was then dried over approximately 2 g anhydrous $MgSO_4$, then dried down, resuspended in 50 ml water and freeze dried. This batch process can be repeated for the entire 25 g of freeze dried slurry liquor.

Five grams of the slurry powder yielded approximately 628 mg ethyl acetate soluble material. By mass the ethyl acetate fraction contained 34% gallic acid and 64% TF.

TF was further purified as follows. A column of SEPHADEX LH20 (SEPHADEX is a trade mark) was washed with one litre of aqueous acetone, followed by one litre absolute alcohol. Approximately 1 g of ethyl acetate soluble material was dissolved in 100% ethanol and loaded onto the column, then eluted with 100% ethanol. Fifty 100 ml fractions were collected. TF containing fractions were identified from their colour (fractions 33–50) and analysed by HPLC.

The fractions were combined, dried down, resuspended in water and freeze dried. Details of the fractions combined, TF yield and TF% purity (as determined by HPLC) are shown in Table 1 below:

TABLE 1

Analysis of fractions

| Fractions | Amount (mg) | % Purity |
|---|---|---|
| 33–36 | 79 | 86.7 |
| 37–40 | 109 | 93.5 |
| 41–43 | 128 | 96 |
| 44–50 | 140 | 98 |

Figure 3:
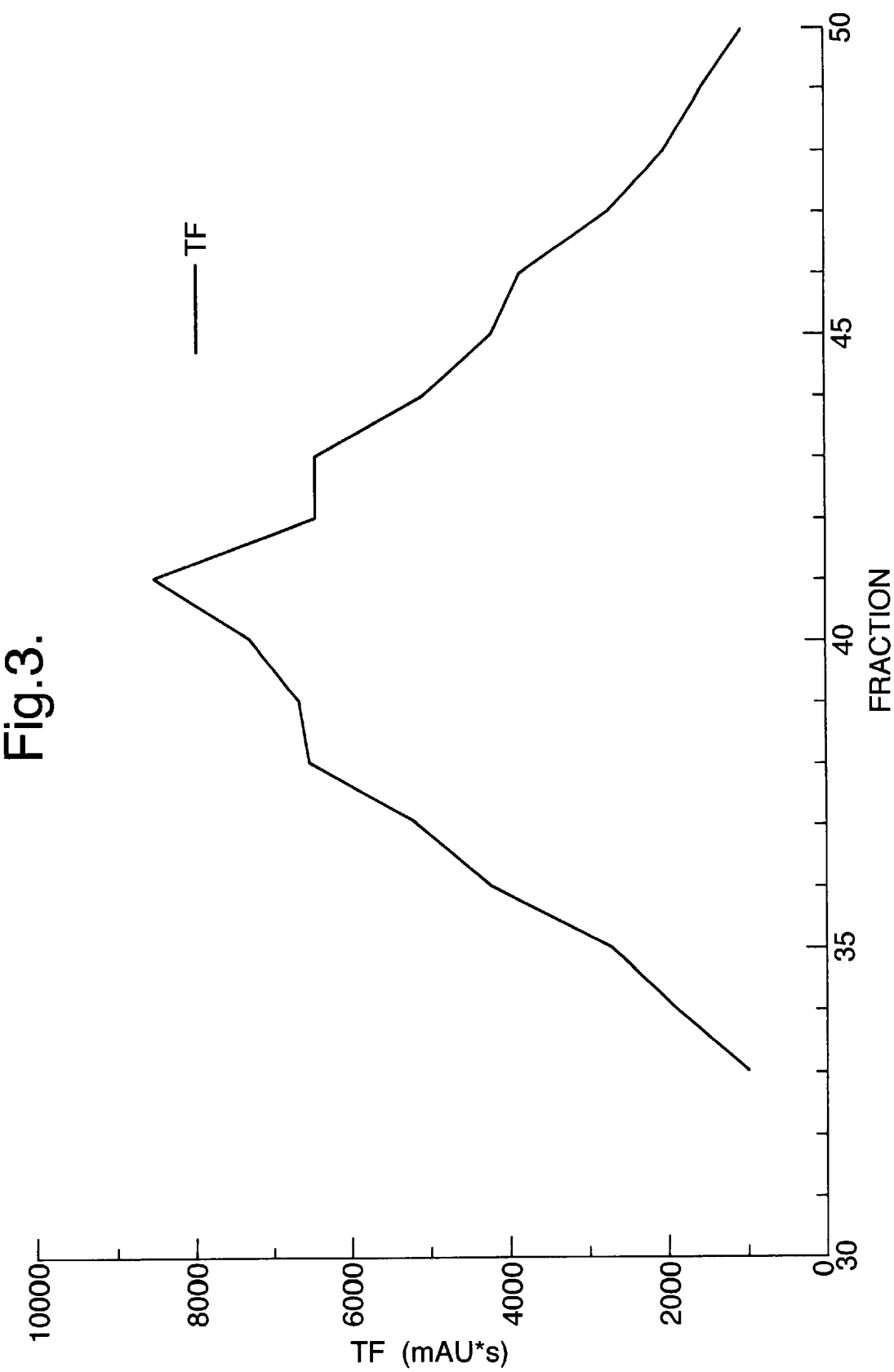
FIG. 3 is a graph of the amount of TF in various fractions eluted from a chromatographic column.

FIG. 3 is a graph illustrating the amount of TF in fractions 33 to 50, measured in mAU*s. This unit represents the peak area of theaflavin in each fraction as determined by HPLC analysis. The peak height is recorded in milliabsorbance units (mAU) and the peak width in seconds, giving an area in mAU*s.

In the example, the fermentation process was not fully optimised for TF production. Only the tannase treatment was optimised to obtain quantitative degallation of catechins. It is possible that other process parameters such as fermentation time, temperature, pH, raw material (in terms of initial catechin composition) could be optimised to maximise TF yield. The yields of TF obtained should therefore be treated as illustrative only. The TF extraction procedure is very efficient.

EXAMPLE 2

Small Scale Fermentation with Tannase Pre-treated Dhool

Raw Material

Dhool was prepared from frozen withered leaf of BBK clone 35 with four passes through the CTC machine and stored frozen at −80° C.

Fermentations

Shake flask slurry fermentations were carried out as follows. Dhool (8 g) was added to 42 ml $H_2O$ in a shake flask and allowed to thaw under a stream of $N_2$ for 10 minutes, with agitation on a magnetic stirrer. KIKKOMAN's (TM) tannase (1 mg/flask) was added and the slurry incubated for a further 60 minutes under $N_2$. After that the flask was transferred to a shaking incubator table and fermented for 75 minutes at 200 rpm. Standard fermentations were carried out in the same way, but without tannase addition or incubation under $N_2$.

Samples (1 ml) were taken from the slurry at the beginning and end of tannase treatment and at 15 minute intervals during the fermentation. These were immediately centrifuged and 200 µl of the supernatant added to 800 µl antioxidant solvent (15% (v/v) acetonitrile, 1.7% (v/v) acetic acid, 1 mM EDTA, 21.2 mM-ascorbic acid prior to HPLC analysis.

Methanol Extraction

Dhool (1 g) was refluxed in 40 ml 70% (v/v) aqueous methanol for 30 minutes. Once cool, the final volume of extract was determined and 200 µl added to 800 µl antioxidant solvent prior to HPLC analysis.

HPLC Analysis

Samples were analysed using an HP1100 HPLC with diode array detection.

In order to investigate chemical changes caused by tannase treatment, small scale (50 ml) fermentations were carried out, with and without tannase treatment, and HPLC analysis was done on untreated dhool (t=0), after 60 minutes suspension with nitrogen sparge (t=60) and after 75 minutes fermentation (t=135). The resulting HPLC traces are shown in FIGS. 4 to 8.

Figure 4:
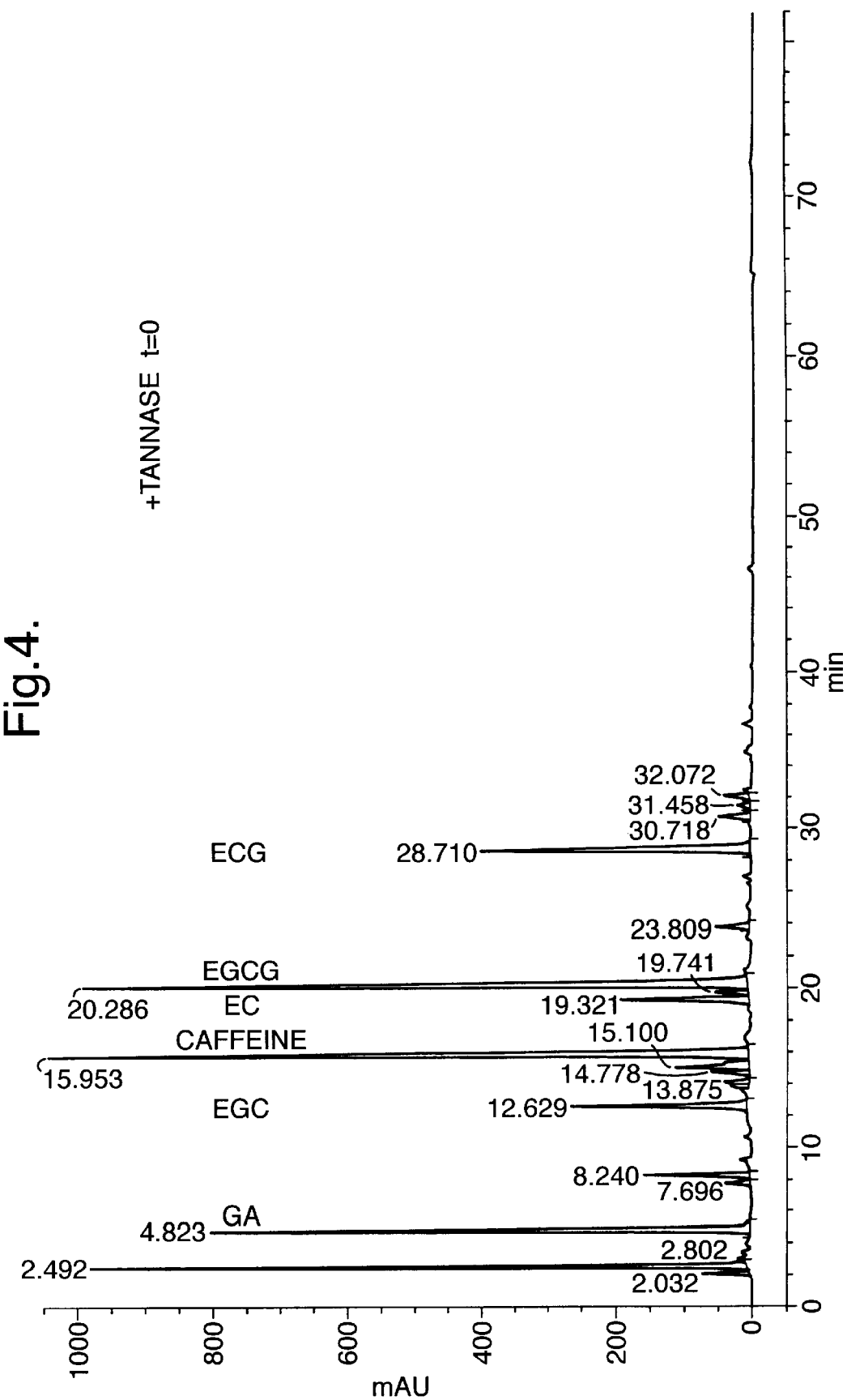
FIGS. 4 to 8 are HPLC traces.

In FIG. 4 (t=0), various peaks are marked as follows:

GA=gallic acid

EGC=epigallocatechin

CAF=caffeine

EC=epicatechin

EGCG=epigallocatechin-3-gallate

ECG=epicatechin-3-gallate

Figure 5:
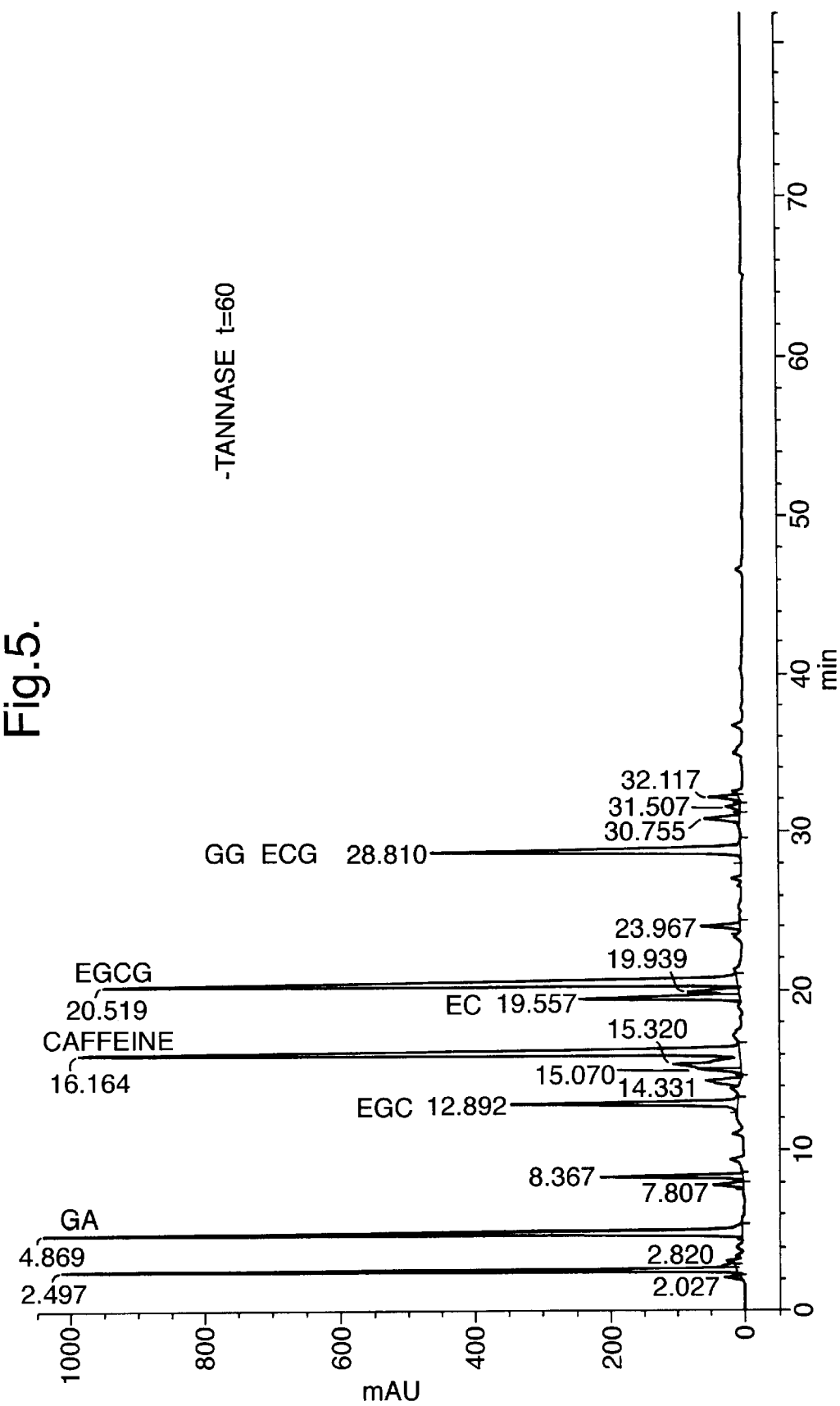
Figure 6:
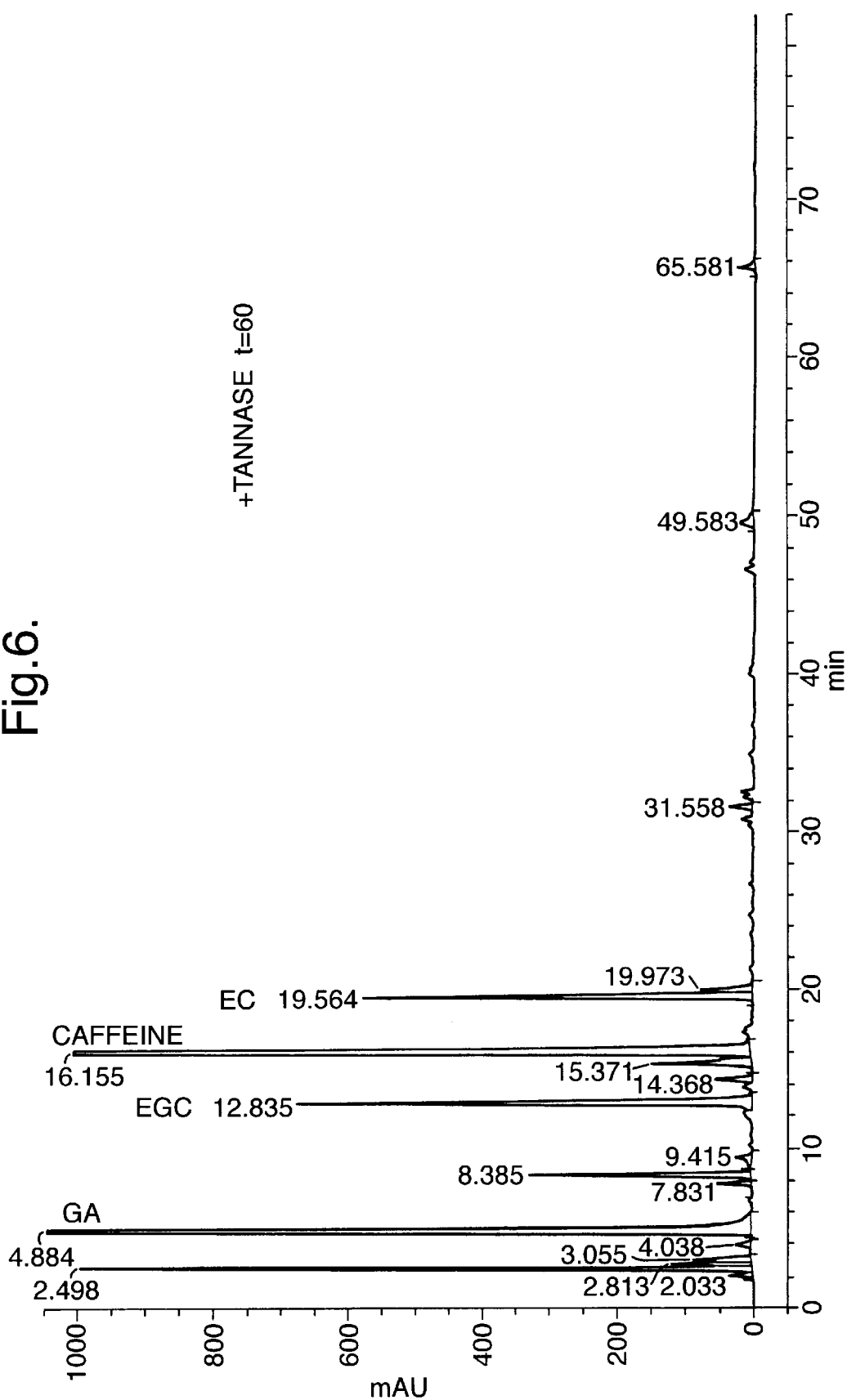

FIGS. 5 and 6 are respective traces after 60 minutes suspension with nitrogen sparge, without and with tannase treatment. In the absence of tannase there is little change in the peaks identified in FIG. 4. In contrast, after tannase treatment there is no ECG or EGCG apparent, but increased peaks for EC, EGC and GA. These results show that complete degallation of the gallated catechins (ECG to EC and EGCG to EGC) is achieved by the tannase treatment used.

Figure 7:
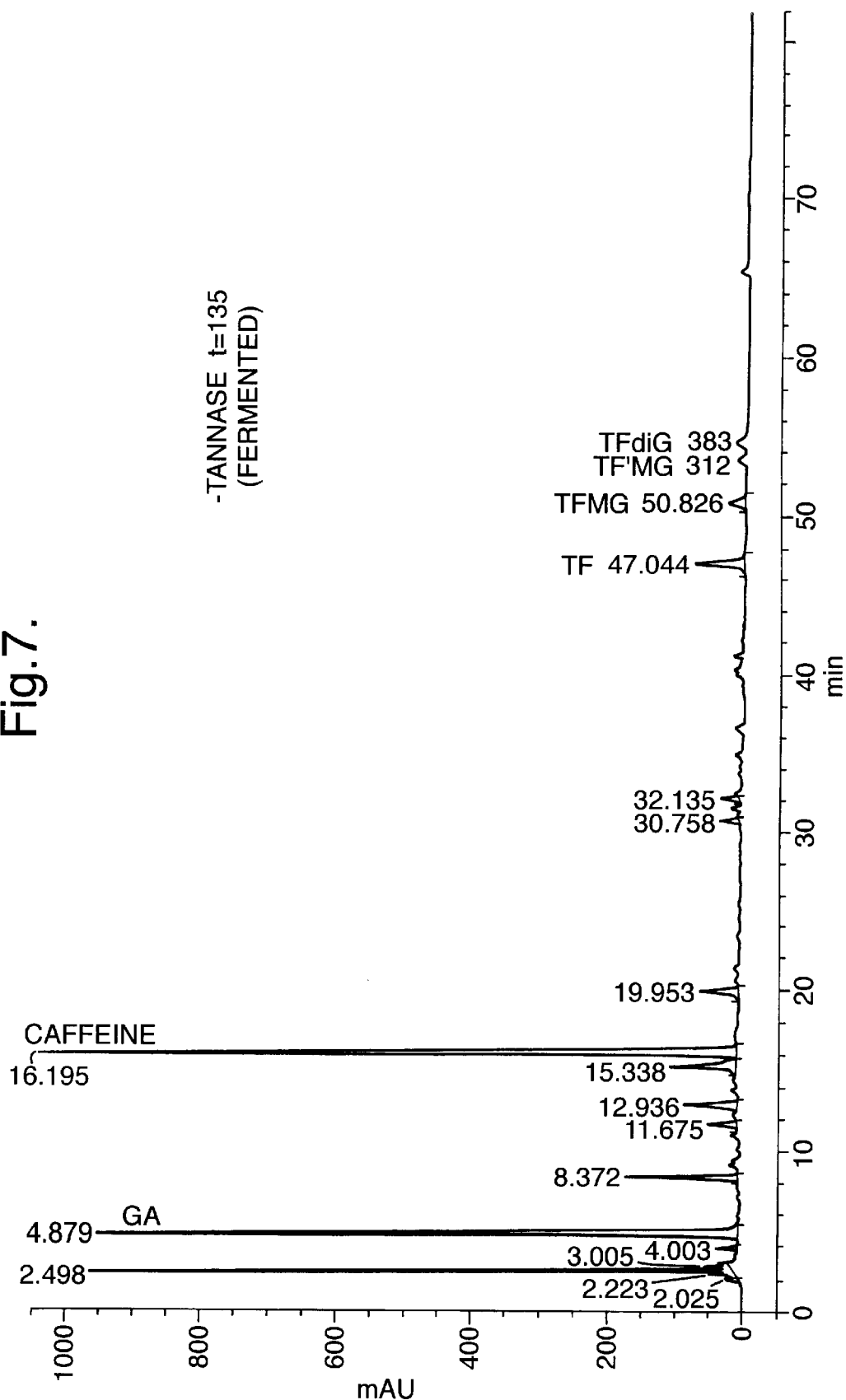
Figure 8:
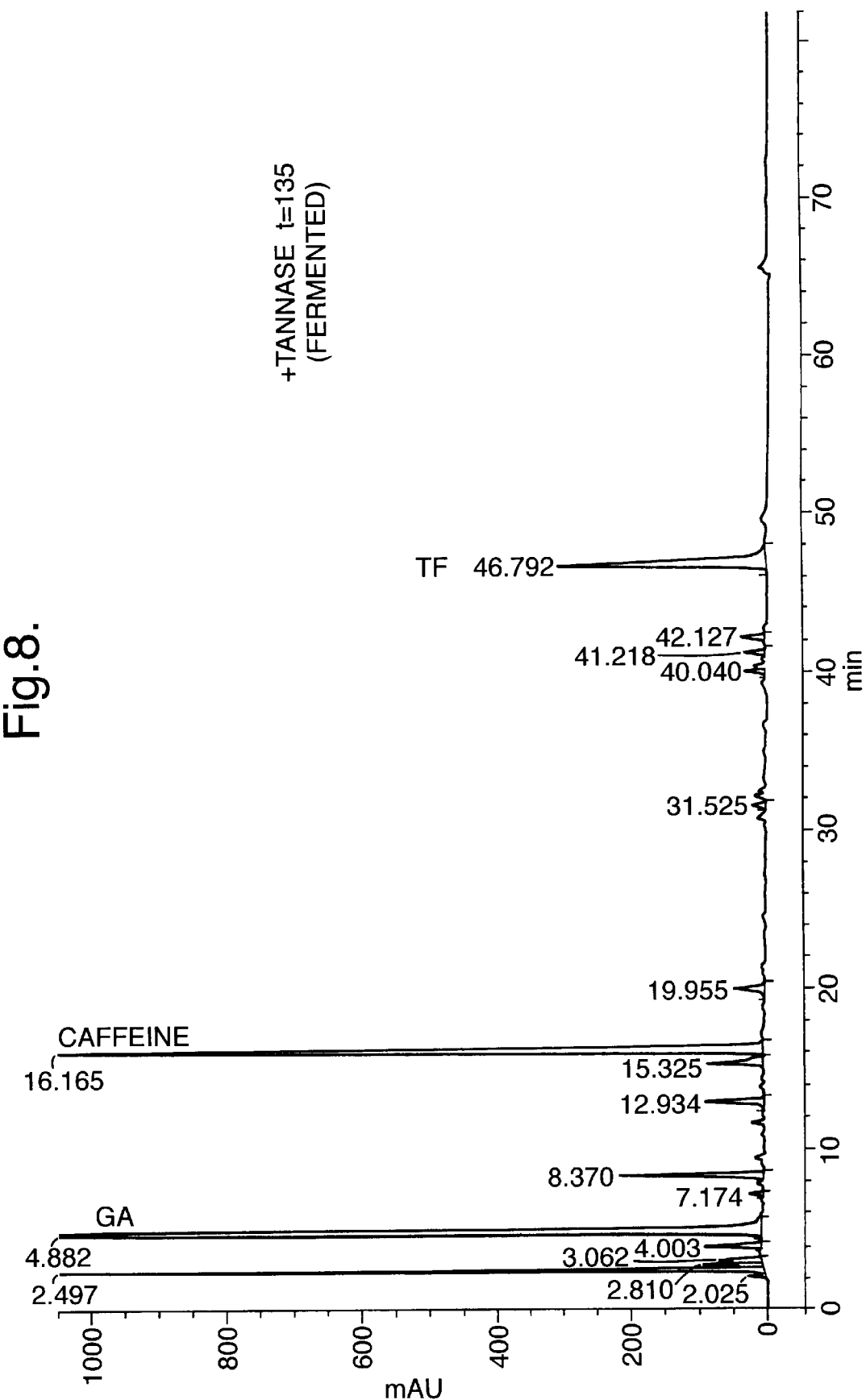

FIGS. 7 and 8 are further traces taken after 75 minutes fermentation following the initial 60 minutes suspension, with FIG. 7 showing results without tannase treatment and FIG. 8 showing results with tannase treatment prior to fermentation. FIG. 7 (t=135, no tannase) shows peaks for the "normal" complement of theaflavins.

TF=theaflavin

TFMG=theaflavin-3-gallate

TF'MG=theaflavin-3'-gallate

TFDiG=theaflavin-3,3'-digallate

In contrast, FIG. 8 (t=135, with tannase treatment) shows formation of TF only. The TF is also present in much higher amounts than in the no tannase treatment sample. Large amounts of gallic acid (GA) are also present after fermentation following tannase treatment.

The results are summarised in Table 2 below, which gives amounts of $\mu mol.g^{-1}$ (FW). In the table, values at t=0 are for solvent-extracted dhool, while other values are the composition of slurry liquor after 5 and 75 minutes fermentation without tannase treatment (−tannase), and after 60 minutes of tannase treatment and 75 minutes post-tannase treatment fermentation (+tannase).

Figure 9:
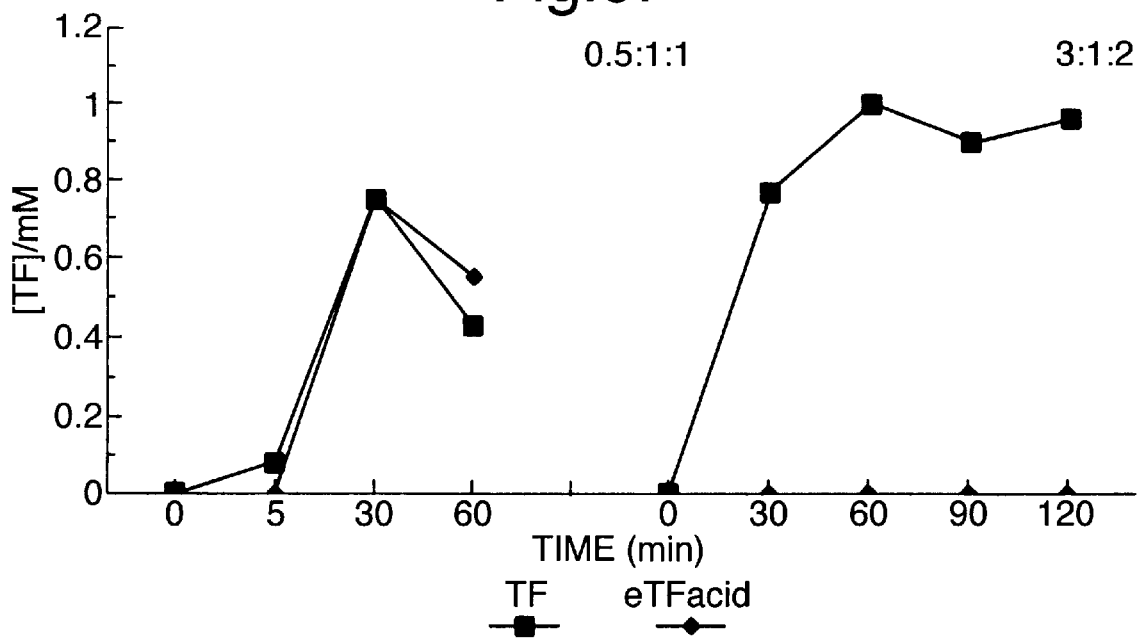
FIG. 9 is a graph showing the amount of theaflavin (TF) and epitheaflavic acid (eTF acid) versus time for different EGC:EC:Ga mixtures.

Experiments were carried out with mixtures of EGC/EC/GA in molar ratios of 3:1:2 and 0.5:1:1, and results are shown in FIG. 9.

These results show that, with a 3:1:2 ratio of EGC/EC/GA (which approximates to the ratios normally found in tannase-treated dhool (see Table 2 of Example 2) the major reaction product obtained is theaflavin and, in fact, no epitheaflavic acid is formed. If, however, the EGC level is reduced, e.g. with a ratio of 0.5:1:1 EGC/EC/GA, then epitheaflavic acid can be formed, and in equal amounts to theaflavin.

The present work thus demonstrates that, contrary to statements in U.S. Pat. No. 3,812,266, the enhanced colour generated during fermentation of tannase-treated dhool is not due to the formation of epitheaflavic acid, but rather to enhanced levels of theaflavin.

EXAMPLE 4

Improved Extraction Procedure

Tannase Pre-treated Fermentation

A variety of alternative methods were tested, on tannase-treated material, in order to increase the extraction efficiency

TABLE 2

Component analysis of slurry liquor during fermentation with and without tannase

| Time (min) | Ga | Caf | EGC | EC | EGCG | ECG | TF | TFMG | TF'MG | TFdiG | EGC:EC:Ga |
|---|---|---|---|---|---|---|---|---|---|---|---|
| 0 (solvent extracted dhool) −tannase | 9 | 60 | 57 | 18 | 48 | 18 | — | — | — | — | 2.9:1:2.1 |
| 5 | 9 | 27 | 21 | 10 | 18 | 6 | — | — | — | — | 2.4:1:2 |
| 75 | 9 | 22 | — | — | — | — | 2 | 0.2 | 0.2 | 0.2 | |
| +tannase | | | | | | | | | | | |
| 60 | 54 | 33 | 67 | 23 | — | — | — | — | — | — | 2.9:1:2.3 |
| 135 | 55 | 32 | — | — | — | — | 22 | — | — | — | |

EXAMPLE 3

Model Oxidations with Varying Substrates

Figure 10:
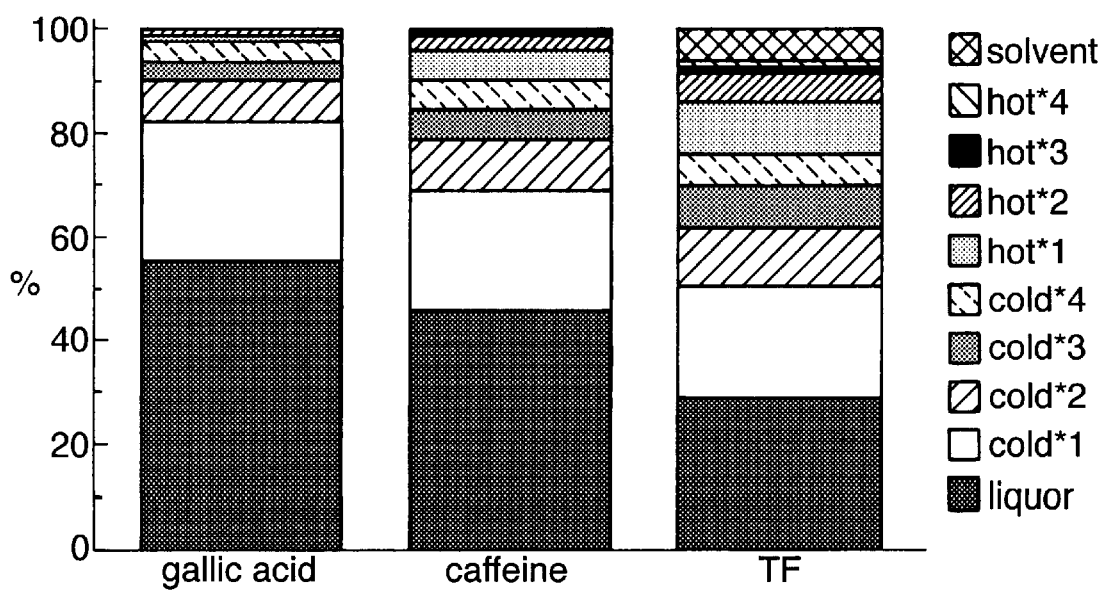
FIG. 10 is a graph showing the component distribution during extraction of tannase pre-treated slurry.

Model oxidation studies were carried out, using defined catechin mixtures with tea leaf extracts. Mixtures of EGC/EC/GA in different proportions were reacted with tea leaf extracts and the amounts of TF and epitheaflavic acid (eTF acid) produced after various times were measured. Catechins, purified from instant green tea, were mixed in various concentrations (total catechin concentration 6 mM) in 1 ml total reaction volume, with phosphate/citrate buffer, pH 5.5 and tea leaf enzyme extract containing 0.05 U polyphenol oxidase (PPO) activity. The enzyme extract was prepared by grinding about 1 g of frozen, withered BBK clone 35 leaf in 50 mM MES (2-[N-morpholino] ethanesulphonic acid) buffer, pH 5.5, 0.3% Triton X-100, 1 M NaCl, 750 mg PVPP (polyvinylpolypyrrolidone), followed by centrifugation and desalting through a PD-10 column (Pharmacia). PPO activity was assayed by measuring $\Delta A_{400}$ of 100 $\mu l$ of desalted extract in 3 ml total volume of phosphate/citrate buffer, adding 75 $\mu l$ 0.2 M catechin to start the reaction (1 U=$\Delta A_{400}$/min of 1.0). The mixture was incubated at 30° C. at 200 rpm on an orbital shaker. Samples were taken at appropriate intervals and reaction terminated by addition into 400 $\mu l$ antioxidant solvent (15% (v/v) acetonitrile, 1.7% (v/v) acetic acid, 250 ppm ascorbic acid, 250 ppm EDTA). Theaflavin and epitheaflavic acid production was then assayed via rp-HPLC.

of components from the dhool. Firstly, a tannase-treated slurry was deleafed through muslin and the residual dhool washed four times with 50 ml cold water, four times with 50 ml boiling water and finally extracted in boiling 70% methanol. This procedure (See FIG. 10) led to the majority of theaflavin (>93%) being extracted by the combination of cold/hot washes. The amount of theaflavin in the first hot wash was greater than that in the last cold wash, and the amount in the solvent extract greater than the last hot extract. This finding demonstrated that the different stages of the extraction were required to extract all the theaflavin i.e. the material that required hot water to be extracted would not come out in cold, nor would the material in the organic solvent fraction come out in hot water.

Other methods tested were as follows:

1. The muslin used to filter the slurry was used as a "tea bag" which was suspended in 200 ml room-temperature water and the dhool allowed to infuse for 10 minutes. After deleafing, the residual dhool was similarly infused in boiling water.

2. As 1 above, but with an additional wash of the dhool after each filtration step.

3. The spent dhool was scraped off the muslin and infused x4 in 50 ml room temperature water followed by x4 in 50 ml boiling water.

4. The spent dhool was scraped off the muslin and infused in 200 ml cold water for 10 minutes. After filtration this was repeated with boiling water.

5. As 4 above but with infusion in 100 ml rather than 200 ml for 10 minutes.

In all cases the residual dhool was then extracted in boiling 70% (v/v) aqueous methanol to extract any residual material.

Figure 11:
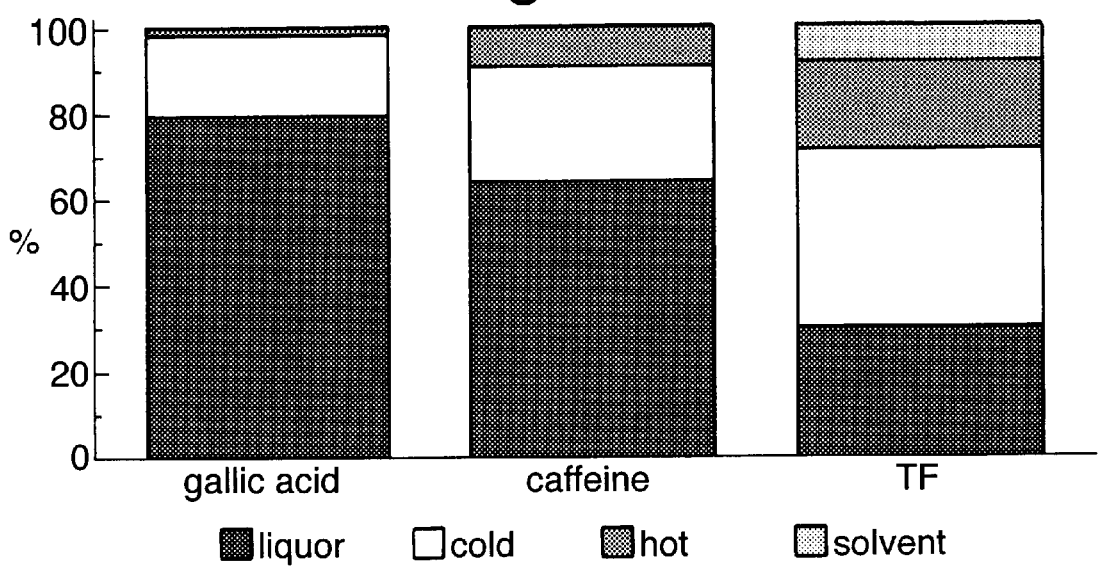
FIG. 11 is a graph showing the component distribution during extraction of tannase pre-treated slurry with the optimal protocol (#5)

All these procedures gave similar results and so method #5, infusion of "loose leaf" dhool in 100 ml cold water, 100 ml hot water and then extraction with methanol (See FIG. 11) was chosen for all further studies, as it gave acceptable results and was the easiest protocol to carry out. With this method >91% of the theaflavin was extracted with water (and >99% of gallic acid/ caffeine). The optimised extraction protocol is as follows:

Extraction

At the end of the fermentation, the slurry was deleafed through 4 layers of muslin, using a Buchner funnel, the volume of the liquor recorded, and a sample taken for HPLC analysis as described above. The residual dhool was then extracted as follows: The dhool was scraped from the muslin, and infused in 100 ml room-temperature water for 10 minutes. This slurry was then filtered through the muslin, the volume of this "cold water" extract recorded and a sample taken for HPLC analysis. The dhool was again scraped from the dhool and infused for 10 minutes in 100 ml boiling water then filtered and this "hot water" extract sampled in the same way as the cold extract. The residual dhool was finally extracted in boiling 70% (v/v) aqueous methanol as described in Example 2.

EXAMPLE 5

Effect of Fermentation Temperature on Theaflavin Yield

Figure 12:
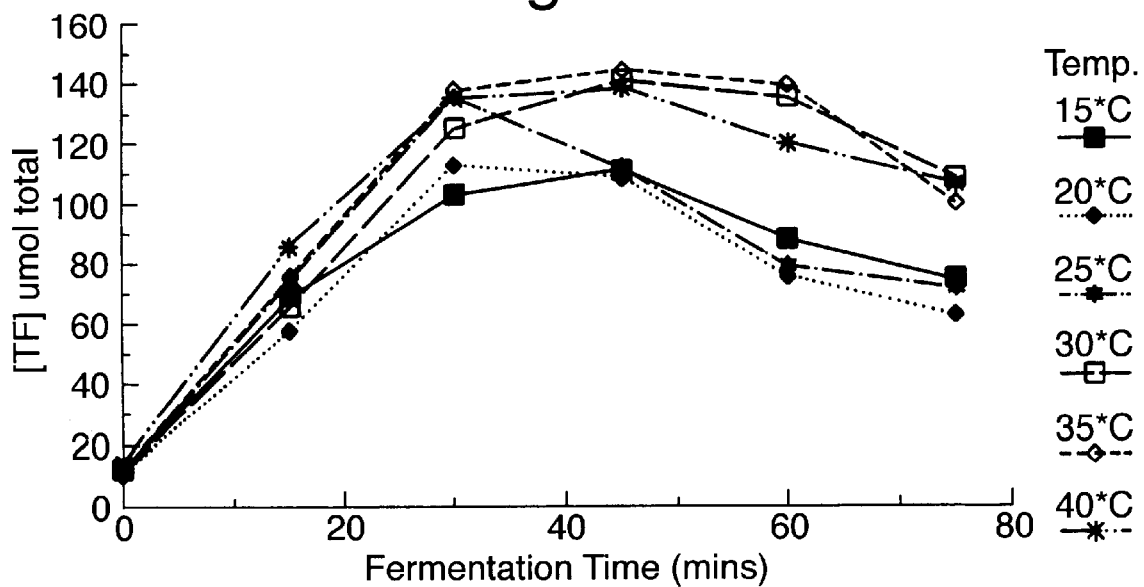
FIG. 12 is a graph showing the effect of temperature on theaflavin formation during fermentation of tannase pre-treated slurry at pH 4.7.

The optimised extraction protocol was then used in a study on the effect of fermentation temperature on the formation of theaflavin in tannase-treated slurry. Samples of the slurry liquor were taken at 15 minute intervals during a 75 minute fermentation to monitor the TF levels in the liquor (See FIG. 12). At the end of the fermentation, the slurry was extracted, as described above, and the total amount of theaflavin in the various fractions determined (See FIG. 13).

a) TF Levels in Liquor

At all temperatures, theaflavin levels in the liquor increased rapidly during the first 30 minutes of fermentation, reaching higher levels at the higher temperatures. Beyond 30 minutes there appeared to be a marked difference between fermentations carried out at 15–25° C. and those at 30 to 40° C. At the lower temperatures, and particularly at 25° C., the theaflavin level in the liquor started to fall rapidly from this peak. In contrast, at higher temperatures, 30 and 35° C., the theaflavin level remained constant until 60 minutes when it started to fall. At 40° C., theaflavin started to fall from 45 minutes and the final liquor level was similar to that found at 30 and 35° C. These results appear to indicate that, at the higher temperatures, theaflavin synthesis is greatest and turnover is lowest, neither of which would be expected.

b) Total TF Extracted from Slurry

Figure 13:
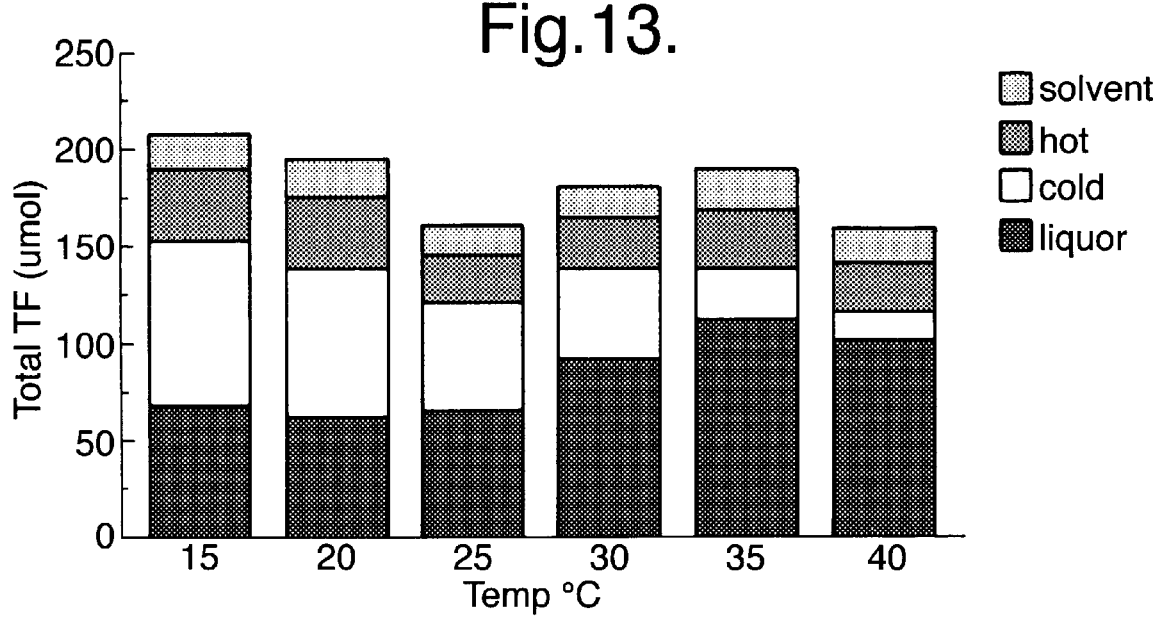
FIG. 13 is a graph showing the effect of temperature on total theaflavin formation during fermentation of tannase pre-treated slurry.

The results of the exhaustive extraction of the slurry at the end of the fermentation (75 minutes) are shown in FIG. 13. It can be seen that the TF measurements of the slurry liquor during fermentation give a misleading picture of total theaflavin formation, since the total levels appear relatively unaffected by temperature (in fact, slightly higher levels at the lower temperatures). The total amounts of theaflavin formed, and the amounts in solvent and hot water fractions are broadly similar at the different temperatures. The major effect of altering fermentation temperature is actually to alter the distribution of theaflavin between the liquor and the cold water (perhaps loosely attached to dhool) fractions. Thus at 15° C. the amount of TF in the liquor was 32%, but this increased to 63% at 40° C. and there was a corresponding decrease in the amount of TF in the cold water fraction from 42% at 15° C. to 10% at 40° C. This shows that the reduction in theaflavin in the liquor, following the peak at 30 minutes fermentation, is due to theaflavin becoming associated with the dhool and not to further oxidation.

EXAMPLE 6

Effect of Fermentation pH on Theaflavin Yield

Figure 14:
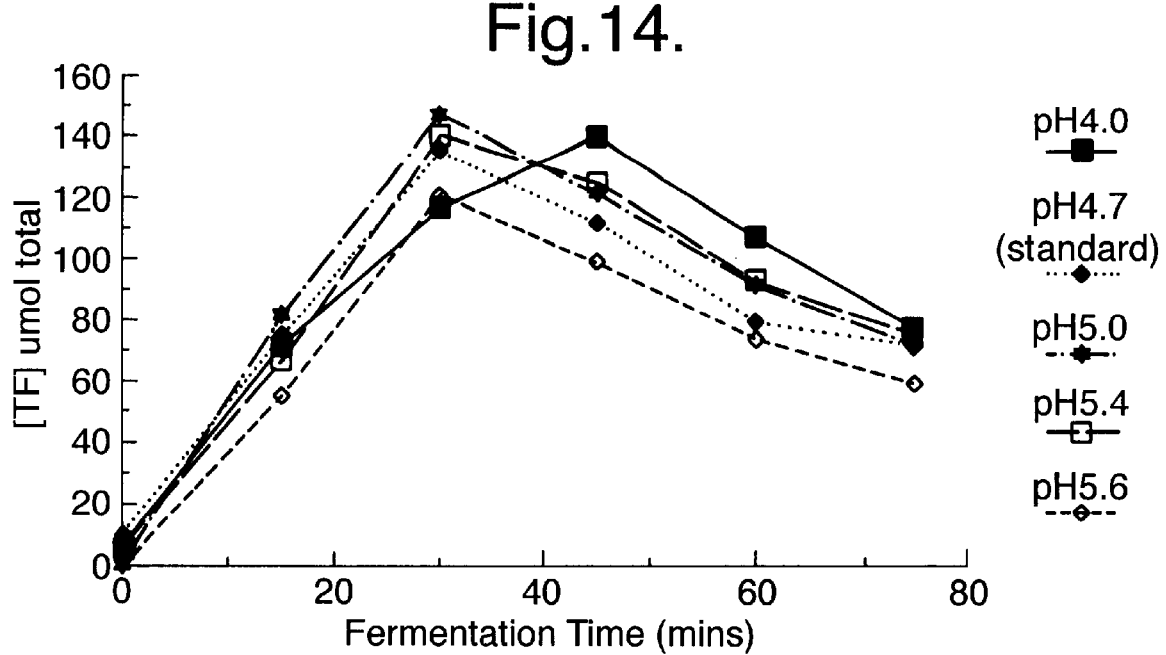
FIG. 14 is a graph showing the effect of pH on theaflavin formation during tannase pre-treated fermentation.
Figure 15:
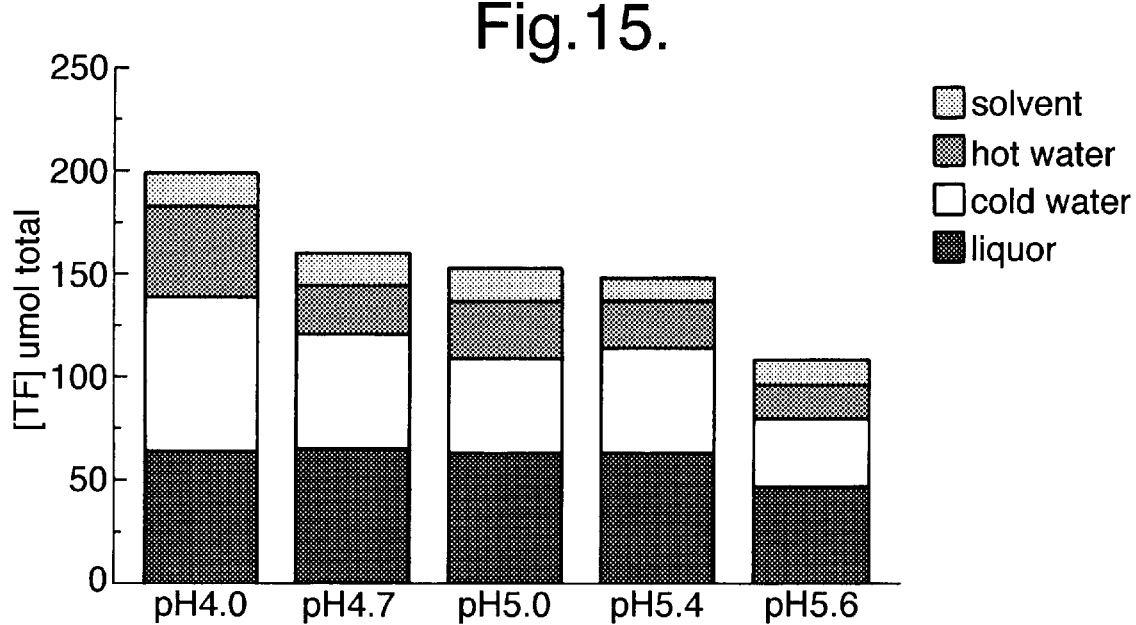
FIG. 15 is a graph showing the effect of initial fermentation pH on total TF formation during tannase pre-treated slurry fermentation.

The inventors investigated the effect of varying fermentation pH between 4.0 and 5.6 on the yield of theaflavin from tannase-treated slurry fermentation. After tannase pre-treatment the pH of the slurry was around 4.7, and this was adjusted by addition of HCl or NaOH. Altering the fermentation pH from 4.0 to 5.4 had little effect on levels of TF present in the liquor (See FIG. 14), but levels were somewhat lower at pH 5.6 (at pH 4.0 the TF peak occurred at 45 minutes rather than 30 minutes). When considering total extractable TF (See FIG. 15) there was little difference between pH 4.7 and 5.4, but levels were somewhat reduced at pH 5.6. However, lowering the pH to 4.0 enhanced total theaflavin yield compared to the 'standard' pH 4.7, with the additional TF being present in the cold/hot washes.

EXAMPLE 8

Characterisation of Cold and Hot Water Wash Fractions

Samples of the liquor, cold water and hot water extracts from a 15° C. and 35° C. tannase treated fermentations were chilled, decreamed and freeze dried and the powders resuspended at equal concentration (0.32% (w/v)). Colour measurements were carried out and the composition, by mass, of each fraction, prior to decream, was determined. The composition of each fraction from the two fermentations was determined by HPLC analysis. These are shown in Tables 3 and 4 respectively while the colour data are shown in Table 5.

TABLE 3

Composition by mass of different fractions obtained from 15° C. tannase pre-treated slurry fermentation

| | Liquor | | Cold | | Hot | |
| --- | --- | --- | --- | --- | --- | --- |
| | mg | % | mg | % | mg | % |
| Gallic acid | 63.6 | 8.4 | 8.8 | 5.3 | 1.2 | 1.2 |
| Caffeine | 43.3 | 5.7 | 15.9 | 9.5 | 9.2 | 9.2 |
| TF | 49.8 | 6.6 | 25.7 | 15.4 | 16.6 | 16.6 |
| Other | 599.5 | 79.3 | 116.2 | 69.7 | 73.1 | 73.0 |
| Total | 756.2 | 10.0 | 166.6 | 100 | 100.1 | 100 |

TABLE 4

Composition by mass of different fractions obtained from 35° C. tannase pre-treated slurry fermentation

|  | Liquor | | Cold | | Hot | |
| --- | --- | --- | --- | --- | --- | --- |
|  | mg | % | mg | % | mg | % |
| Gallic acid | 78.1 | 9.5 | 12.1 | 8.9 | 1.2 | 1.6 |
| Caffeine | 53.3 | 6.5 | 13.3 | 9.8 | 6.0 | 8.1 |
| TF | 61.8 | 7.5 | 11.6 | 8.6 | 13.3 | 18.1 |
| Other | 631.4 | 76.6 | 98.8 | 72.8 | 53.1 | 72.1 |
| Total | 824.6 | 100 | 135.8 | 100 | 73.6 | 100 |

TABLE 5

Colour comparison of the fractions obtained during extraction of slurry fermentations

| 0.32% solids | L | a | b |
| --- | --- | --- | --- |
| 1) 15° C. tannase | | | |
| Liquor | 88.5 | 1.5 | 82.3 |
| Cold | 67.0 | 22.4 | 103.4 |
| Hot | 59.6 | 26.3 | 96.7 |
| 2) 35° C. tannase | | | |
| Liquor | 85.1 | 4.2 | 81.8 |
| Cold | 70.1 | 15.2 | 92.2 |
| Hot | 62.9 | 29.9 | 101.5 |

In each case, the material in the cold and hot water extracts contains a higher proportion of theaflavin than the liquor, for example, the hot water extracts contained about 2.5 fold higher levels of TF, on a percentage basis, than the liquors. Although the absolute amounts of solids in the cold and hot water extracts are lower than that in the liquor, they are still very significant, representing an additional 35% for the 15° C. tannase fermentation and 25% for the 35° C. tannase fermentation. Table 5 shows that, at equivalent solids levels, the cold and hot water fractions are markedly darker (lower L* value), redder (higher a* value) and more yellow (higher b* value) than their corresponding liquors.

To determine whether the additional extracted material would make a difference to the colour of the final slurry powder, a comparison was made of the colour properties of the powders prepared from individual fractions with a powder prepared by extracting the spent dhool twice with hot water and combining with the liquor prior to decreaming and freeze drying. The composition of the individual fractions and the powders are given Table 6 below. The colours of the individual powders and the mixture are given in Table 7 which is also below.

TABLE 6

Comparison of composition of extracts and freeze dried powders from tannase pre-treated fermentation at 15° C.

| mg | Ga | Caf | TF | Total |
| --- | --- | --- | --- | --- |
| A) Composition of extracts | | | | |
| Liquor | 53.3 | 30.2 | 41.4 | — |
| Cold | 14.0 | 12.3 | 32.2 | — |
| Hot | 0.0 | 2.8 | 11.3 | — |
| Total | 67.3 | 45.3 | 84.9 | — |
| mix | 66.6 | 42.8 | 84.3 | — |

TABLE 6-continued

Comparison of composition of extracts and freeze dried powders from tannase pre-treated fermentation at 15° C.

| mg | Ga | Caf | TF | Total |
| --- | --- | --- | --- | --- |
| B) Composition of powders | | | | |
| Liquor | 36.2 | 19.8 | 16.3 | 390 |
| Cold | 9.6 | 10.3 | 21.9 | 150 |
| Hot | 1.2 | 2.1 | 6.9 | 50 |
| Total | 47.0 | 32.2 | 45.1 | 590 |
| mix | 45.8 | 33.3 | 50.8 | 570 |

TABLE 7

Colour comparison of fractions from tannase pre-treated fermentation at 15° C. with combined fractions

| 0.32% (w/v) | Yield (mg) | L* | a* | b* | C | h |
| --- | --- | --- | --- | --- | --- | --- |
| Natural pH | | | | | | |
| Liquor | 390 | 85.8 | 4.3 | 85.0 | 85.1 | 87.1 |
| Cold extract | 150 | 63.7 | 28.5 | 101.8 | 105.7 | 74.4 |
| Hot extract | 50 | 66.8 | 30.1 | 107.3 | 111.5 | 74.4 |
| Mix | 570 | 75.2 | 18.3 | 104.2 | 105.8 | 80.1 |
| pH 3.7 | | | | | | |
| Liquor | | 87.8 | 1.8 | 81.9 | 81.9 | 88.8 |
| Cold extract | | 66.0 | 26.5 | 104.4 | 107.7 | 75.8 |
| Mix | | 78.1 | 15.6 | 105.0 | 106.1 | 81.7 |

The colour values show that recovery of the additional coloured material does make a substantial difference (L 10 units darker, a* 14 units redder and b* 19 units yellower) to the colour of the cold water soluble powder that can be prepared from slurry fermentation. The compositional data show that there is appreciable loss of material during tea powder preparation (4° C. chill overnight, centrifugation at 4° C. and freeze dry) e.g. 40% TF for the mixture. However, the powder prepared from the mixed fraction still contains 9% TF compared to 4% TF in the liquor only powder. It is therefore evident that addition of the cold and hot water washes to the slurry liquor itself can make a substantial difference to the final characteristics, and probable cost effectiveness, of powders prepared via slurry fermentation.

EXAMPLE 8

Effect of Decream Conditions on Theaflavin Recovery

Tea Powder Preparation

Samples were chilled overnight (4° C.) then centrifuged, 15,000 g for 15 minutes, and filtered through WHATMAN™ No 54 paper. The filtrates were frozen using a dry ice/acetone bath and freeze dried. The powders were resuspended at 0.32% (w/v) in distilled water and colour determined using a MINOLTA™ CT-210 colourimeter.

The inventors determined the effect of time at 4° C. prior to centrifugation in order to investigate whether prolonged, overnight, chill was leading to unnecessary losses of TF during standard decream. Aliquots from an extracted slurry were either centrifuged immediately at 4° C. or chilled for 1 hour, or overnight, prior to centrifugation. Although the differences between the treatments were small (See Table 8 below), immediate centrifugation gave a cold water soluble powder with higher a*, and highest TF content (11.7% by mass of powder). The recovery of TF from the extract in the powder was 91% if centrifuged immediately compared to 77% following overnight chill.

TABLE 8

Effect of chill time prior to centrifugation on recovery of TF with cold decream

| Time prior to centrifuging | Colour at 0.32% solids | | | % TF recovery | % TF g/g powd | TF yield g/kg (FW) dhool |
|---|---|---|---|---|---|---|
| at 4° C. | L* | a* | b* | | | |
| Immediate | 78.2 | 19.2 | 109.6 | 91 | 11.7 | 11 |
| 1 hr chill | 78.2 | 17.4 | 107 | 84 | 11.4 | 10.2 |
| Overnight | 77.2 | 17.9 | 105 | 77 | 10.5 | 9.4 |

The results indicated that immediate centrifugation minimises TF loss, whilst still producing a powder that is entirely soluble in cold water. If the loss of TF during prolonged chill is due to oxidation rather than complexation, then it might be possible to retain TF with addition of ascorbic acid or through metal ion complexation.

What is claimed is:

1. A method for making a theaflavin-rich cold water soluble tea product comprising the steps of treating a slurry of green leaf tea with tannase, fermenting said slurry, deleafing said slurry to give a theaflavin-rich tea liquor and spent dhool, drying said tea liquor to yield a liquor-derived theaflavin-rich cold water soluble tea powder, performing one or more solvent extractions of said spent dhool, drying said extract or extractions to form a dhool-derived theaflavin-rich powder or powders, and mixing said liquor-derived theaflavin-rich cold water soluble tea powder with said dhool-derived theaflavin-rich powder or powders to yield the theaflavin-rich cold water soluble tea product.

2. A method according to claim 1, wherein said theaflavin-rich tea liquor is mixed with said extract or extracts of said spent dhool and that mixture is dried to form the theaflavin-rich cold water soluble tea product.

3. A method for purifying theaflavin comprising the steps of treating a slurry of green leaf tea with tannase, fermenting said slurry, deleafing said slurry to give a theaflavin-rich tea liquor and spent dhool, drying said tea liquor to yield a liquor-derived theaflavin-rich cold water soluble tea powder, performing one or more solvent extractions of said spent dhool, drying said extract or extractions to form a dhool-derived theaflavin-rich powder or powders, mixing said liquor-derived theaflavin-rich cold water soluble tea powder with said dhool-derived theaflavin-rich powder or powders to give a theaflavin-rich cold water soluble tea product, resuspending said tea product in water, extracting said resuspended product with an organic solvent, and passing said extracted product through a chromatographic column that elutes theaflavin.

4. A method according to claim 3, wherein said theaflavin-rich tea liquor is mixed with said extract or extracts of said spent dhool and that mixture is dried to form the cold water soluble tea product.

5. A method according to claim 1 wherein said slurry is treated with tannase in an amount of at least about 3200 tannase activity units/kg tea solids for about 60 minutes at about 25° C.

6. A method according to claim 1 wherein slurry fermentation is carried out at pH in the range 4.0 to 5.5, at a temperature in the range 15 to 30° C. for a time in the range 30 to 75 minutes.

7. A method according to claim 1 wherein the green leaf tea has an EGC (G): EC(G) ratio of about 3:1.

8. A method according to claim 1, wherein the solvent is selected from water and organic solvents.

9. A method according to claim 8, wherein the solvent is water having a temperature between 15 and 25° C.

10. A method according to claim 8, wherein the solvent is water having a temperature between 90 and 100° C.

11. A method according to claim 1, wherein the spent dhool is extracted for a first time using water having a temperature between 15 and 25° C., for a second time using water having a temperature between 90 and 100° C., and for a third time using an organic solvent.

* * * * *